United States Patent [19]

Karjalainen et al.

[11] Patent Number: 5,026,868
[45] Date of Patent: Jun. 25, 1991

[54] INDENYL IMIDAZOLES

[75] Inventors: Arja L. Karjalainen; Arto J. Karjalainen, both of Oulu, Finland

[73] Assignee: Farmos-Yhtyma Oy, Turku, Finland

[21] Appl. No.: 431,959

[22] Filed: Nov. 6, 1989

Related U.S. Application Data

[62] Division of Ser. No. 49,882, May 14, 1987, Pat. No. 4,933,359.

[30] Foreign Application Priority Data

May 15, 1986 [FI] Finland .................................. 862039
Feb. 4, 1987 [FI] Finland .................................. 870462

[51] Int. Cl.[5] .......................................... C07D 233/56
[52] U.S. Cl. .......................................... 548/346
[58] Field of Search .......................................... 548/346

[56] References Cited

U.S. PATENT DOCUMENTS 4,464,358  8/1984  Cox .................................... 424/177
4,689,339  8/1987  Karjalainen et al. ................ 548/336

FOREIGN PATENT DOCUMENTS 0030749  6/1981  European Pat. Off. .
0056271  7/1982  European Pat. Off. .
0165628 12/1985  European Pat. Off. .
0183492  6/1986  European Pat. Off. .

OTHER PUBLICATIONS

Chemical Abstracts, 105:218736c (1986), Scheinin, H., et al.
Eur. J. Pharmacol., 1986, 129 (1–2), 113–21.
Chemical Abstracts, vol. 72, No. 5, Feb. 2, 1970.

Primary Examiner—Mary C. Lee
Assistant Examiner—Robert C. Whittenbaugh
Attorney, Agent, or Firm—Armstrong, Nikaido, Marmelstein, Kubovcik & Murray

[57] ABSTRACT

The invention provides 4(5)-substituted imidazole derivatives of formula

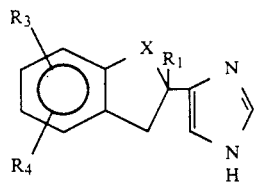

and their acid addition salts, in which either X is —$CH_2$— and $R_1$ is —CN, —COOH, COO(lower alkyl), —CHO, —CO(lower alkyl), lower alkyl of 3 or 4 carbon atoms, lower alkenyl, or lower (hydroxy alkyl) or X is

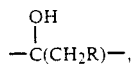

—C(:CH—R)— or —CH($CH_2$R)—, where R is hydrogen or lower alkyl, and $R_1$ is lower alkyl, and $R_3$ and $R_4$ are each hydrogen, methyl, ethyl, methoxy, or halogen, and novel intermediates and processes for their preparation. These compounds, in particular when $R_1$ is lower alkyl, lower alkenyl, or lower (hydroxy alkyl), possess valuable pharmacological properties and are useful especially as selective $\alpha_2$-receptor antagonists.

1 Claim, No Drawings

INDENYL IMIDAZOLES

This invention relates to 4(5)-substituted imidazole derivatives, methods for their preparation, and intermediates for use therein.

The imidazole derivatives of this invention may be represented by the general formula

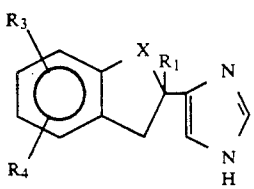

in which either X is —CH$_2$— and R$_1$ is —CN, —COOH, COO(lower alkyl), —CHO, —CO(lower alkyl), lower alkyl of 3 to 5 carbon atoms, lower alkenyl, or lower (hydroxy alkyl) or X is

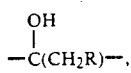

—C(:CH—R)— or —CH(CH$_2$R)—, where R is hydrogen or lower alkyl, and R$_1$ is lower alkyl, and R$_3$ and R$_4$ are each hydrogen, methyl, ethyl, methoxy, or halogen. (The word "lower" as used herein in the terms lower alkyl, lower alkenyl, lower alkenylidene and lower (hydroxy alkyl) means that the radical in question contains not more than 5 carbon atoms.) This formula includes both intermediates and final products. The compounds in which R$_1$ is lower alkyl, lower alkenyl and lower (hydroxy alkyl) and X is —CH$_2$—, —C(:CH—R) and —CH(CH$_2$R)— are potent and selective α$_2$-receptor antagonists. They may be represented by the formula:

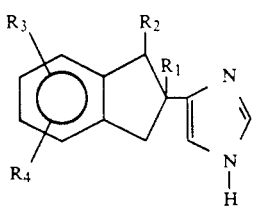

wherein R$_1$ is lower alkyl, OH-substituted lower alkyl or lower alkenyl, R$_2$ is H, lower alkyl, lower alkenyl or lower alkenylidene, R$_3$ is H, CH$_3$, CH$_2$CH$_3$, OCH$_3$ or Hal, and R$_4$ is H, CH$_3$, CH$_2$CH$_3$, OCH$_3$ or Hal, and Hal is halogen. The compounds of the invention are novel except when X is CH$_2$ (R$_2$ is hydrogen) and R$_1$ is methyl or ethyl.

The salts of the compounds of the invention and especially the non-toxic pharmaceutically acceptable acid salts of the compounds of formula I, are within the scope of the invention. The compounds of the invention form acid addition salts with both organic and inorganic acids. They can thus form many pharmaceutically usable acid addition salts, as, for instance, chlorides, bromides, sulfates, nitrates, phosphates, sulphonates, formates, tartrates, maleates, citrates, benzoates, salicylates, ascorbates and the like.

The invention includes within its scope pharmaceutical compositions comprising at least one of the compounds of formula (I) or a non-toxic, pharmaceutically acceptable salt thereof, and a compatible pharmaceutically acceptable carrier therefor.

Adrenergic receptors are physiologically active binding sites which are specific to noradrenaline and adrenaline and are located on the surface of the cell membrane. The adrenoceptors of the sympathetic nervous system have been classified into two different subtypes, alpha- (α) and beta- (β) receptors, which can both be further divided into two subgroups, i.e. α$_1$ and α$_2$ and β$_1$ and β$_2$. Of these receptor types, β$_1$, β$_2$ and α$_1$ are mainly located postsynaptically on the surface of, e.g., smooth muscle and thus mediate, e.g., smooth muscle contraction or relaxation, whereas α$_2$ receptors are mainly located presynaptically on the terminals of noradrenergic nerves. If α$_2$ receptors are stimulated by noradrenaline under physiological conditions, noradrenaline release is blocked, i.e. there is a negative feedback phenomenon.

In addition to the effect caused by noradrenaline, this negative feed-back phenomenon may be induced by certain synthetic α$_2$-agonists, e.g. detomidine and some of its near analogues. The primary pharmacodynamic effects of detomidine, e.g. sedation, have also been proved to be due to its ability to stimulate α$_2$-receptors (Virtanen et al., Progress in Neuro-Psychopharmacology and Biological Psychiatry, suppl. 1983, p. 308).

A selective α$_2$-antagonist may therefore be predicted to be of use in, e.g., diseases which are believed to be connected with deficiency of noradrenalin available in the postsynaptic adrenoceptors of the central and/or peripheral nervous system. These diseases include e.g. endogenous depression and asthma.

Glucose and lipid metabolism are regulated by an inhibitory mechanism involving α$_2$-receptors. Thus α$_2$-antagonists may also be useful in the treatment of metabolic diseases like diabetes and obesity.

Presynaptic α$_2$-receptors also take part in platelet aggregation. It has been shown that α$_2$-agonists activate, and α$_2$-antagonists inhibit, human platelet aggregation (Grant & Schutter, Nature 1979, 277, 659). Thus α$_2$-antagonists may be useful clinically in pathogenic states involving increased platelet aggregation, e.g. migraine. The acute effects of ergotamine, a classical therapeutic agent against migraine, are regarded as being due to its α$_1$-agonist effect. Thus compounds with both antagonist effects on α$_2$-receptors and agonist effects on postsynaptic α$_1$-receptors may have great advantages in the acute and preventive treatment of migraine.

According to the invention the new compounds of the formula:

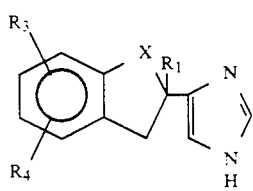

in which either X is —CH$_2$— and R$_1$ is —CN, —COOH, COO(lower alkyl), —CHO, —CO(lower alkyl), ), lower alkyl of 3 to 5 carbon atoms, lower alkenyl, or lower (hydroxy alkyl) or X is

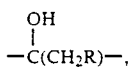

—C(:CH—R)— or —CH(CH$_2$R)—, where R is hydrogen or lower alkyl, and R$_1$ is lower alkyl, and R$_3$ and R$_4$ are each hydrogen, methyl, ethyl, methoxy, or halogen are made by a process which comprises, when X is

—C(:CH—R)—, or —CH(CH$_2$R)—, where R is hydrogen or lower alkyl, R$_1$ is lower alkyl, and R$_3$ and R$_4$ are as hereinbefore defined are made by reacting an imidazole compound of the formula:

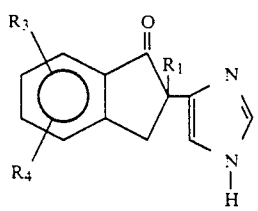

in which R$_1$, R$_3$ and R$_4$ are as hereinbefore defined with an alkyl magnesium halide of formula RCH$_2$Mg—Hal in which R is as hereinbefore defined, to give a product in which X is

and optionally dehydrating the said product to give a compound in which X is —C(:CH—R)—, and optionally reducing the said compound to give a product in which X is —CH(CH$_2$R)—; or, when X is —CH$_2$—, R$_1$ is —CN, —COOH, —COO(lower alkyl), —CHO, —CO(lower alkyl), lower alkyl, lower alkenyl, or lower (hydroxy alkyl) and R$_3$ and R$_4$ are as hereinbefore defined, by reacting an indene derivative of formula:

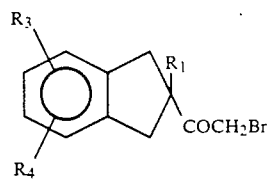

in which R$_1$, R$_3$ and R$_4$ are as hereinbefore defined, with formamide, and optionally converting the radical R$_1$ in the product obtained into another radical within the definition of R$_1$.

This process may be operated in a variety of ways depending on the starting materials and desired end products. Preferred methods are as follows.

Method A

In this method, a 2-(imidazol-4(5)-yl-2-alkyl-1-indanone, as described in European patent application publ. No. 183492, and of the formula:

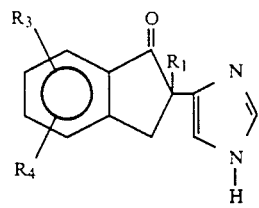

wherein R$_1$ is lower alkyl and R$_3$ and R$_4$ are as defined above, is reacted with an alkylmagnesiumhalide of formula R$_2$MgHal to give a 4(5)-(1,2-dialkyl-2,3-dihydro-1-hydroxy-1H-inden-2-yl)imidazole of the formula

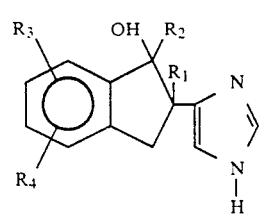

where R$_2$ is a lower alkyl group. Suitable solvents for the reaction are ethers such as diethylether, dibutylether or tetrahydrofuran. The reaction can easily be performed at room temperature.

Dehydration of the compound of formula (III), e.g. by heating with potassium hydrogen sulfate or in acidic water, gives a 4(5)-(2-alkyl-1-alkenyl-2,3-dihydro-1H-inden-2-yl)imidazole of the formula

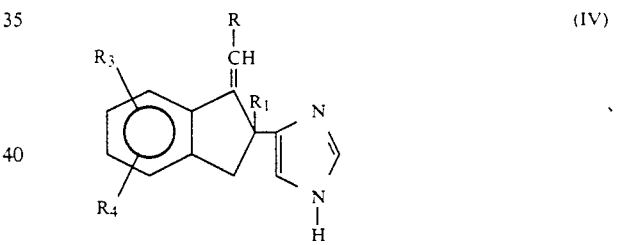

where R is hydrogen or alkyl of up to 3 carbon atoms.

Catalystical hydrogenation of the double bond in the compound of formula (IV) gives a compound of formula (I) in which R$_2$ is lower alkyl.

Method B

A starting material for this method is made by reacting an alkali metal salt, e.g. the sodium salt, of acetoacetic acid ethyl ester, which has the formula

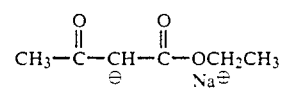

with α, α'-dibromo-ortho-xylene of the formula

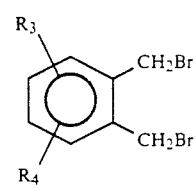

to give 2-acetyl-2,3-dihydro-1H-indene-2-carboxylic acid ethyl ester, which has the formula

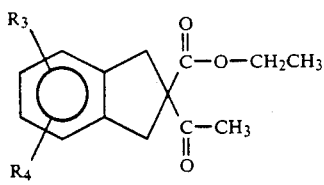
(VII)

Alternatively other alkyl esters, e.g. the methyl ester, of acetoacetic acid can be used.

The compound of formula (VII) is then brominated, e.g. with bromine in a solvent which, for example, can be methylene chloride or methanol. The reaction temperature can vary from room temperature to +60° C. The brominated intermediate, which has the formula

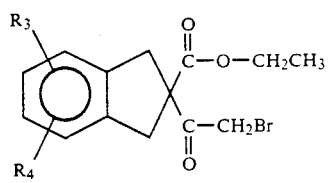
(VIII)

is then reacted with formamide in excess at 170°-180° C. to give 4(5)-(2,3-dihydro-2-ethyloxy-carbonyl-1H-inden-2-yl)imidazole, which has the formula:

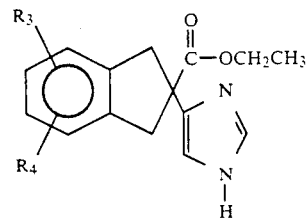
(IX)

Compounds of the invention (I) can be prepared from the compounds of formula (IX) in various ways. The compound can, for example, be hydrolysed to the corresponding acid of the formula:

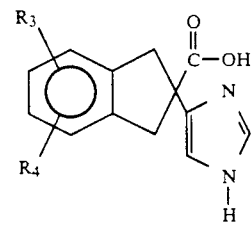
(X)

which is then reduced to the aldehyde of formula:

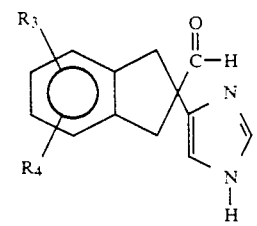
(XI)

Reacting the aldehyde of formula (XI) with an alkyl magnesium halide of the formula $R_5MgHal$ where $R_5$ is an alkyl group, and dehydrating the intermediate of formula:

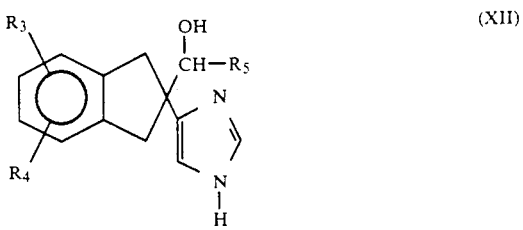
(XII)

for example by heating with potassium hydrogen sulfate, gives a compound of formula (I) where the 2-substituent $R_1$ is an alkenyl group. This alkenyl group can optionally be hydrogenated to an alkyl group, e.g. with hydrogen in the presence of a hydrogenation catalyst such as palladium on charcoal. The reaction may be effected at ambient temperature and pressure. This constitutes an especially convenient route to compounds of formula I in which $R_1$ is alkenyl.

From the intermediate of formula (IX) it is also possible to synthesize 2-alkenyl derivatives according to the invention by reacting the compound of formula (IX) with an alkyl magnesium halide at 20°-50° C. in an appropriate ether such as tetrahydrofuran to give a compound of formula:

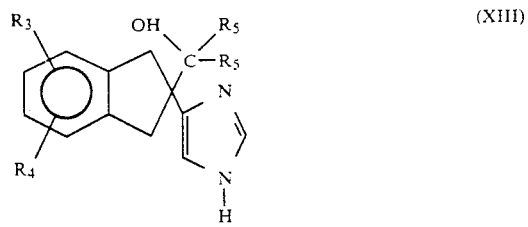
(XIII)

which is then dehydrated, e.g. by heating in the presence of potassium hydrogen sulfate, to give an alkenyl compound of the formula:

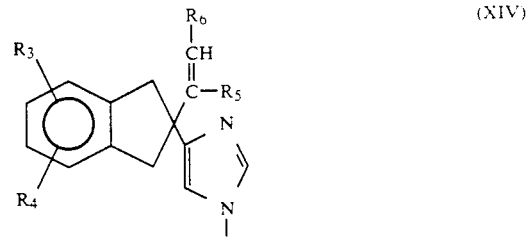
(XIV)

where $R_6$ is H or alkyl, which can optionally be hydrogenated in the manner already described to give a corresponding alkyl compound.

Method C

The starting materials for this method can be obtained by reaction of acetoacetonitrile of formula

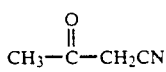 (XV)

and an α, α'-dibromo-o-xylene of formula (VI). This reaction gives a 2-acetyl-2,3-dihydro-1H-indene-2-carbonitrile of the formula:

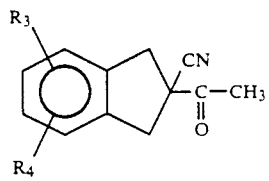 (XVI)

which is then brominated, e.g. with bromine in methanol, to give a 2-bromoacetyl-2,3-dihydro-1H-indene-2-carbonitrile of the formula:

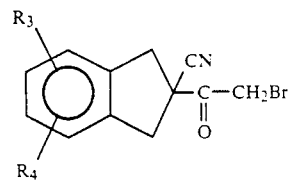 (XVII)

which is then condensed with formamide preferably at 160°–180° C. to give an imidazole derivative of formula:

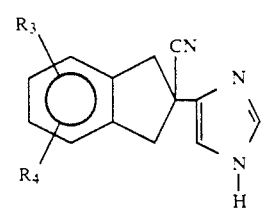 (XVIII)

This nitrile may be converted into a compound of formula (I) by reacting it with an alkyl magnesium bromide of formula $R_5MgHal$ in tetrahydrofuran to give a 2-acyl derivative of formula:

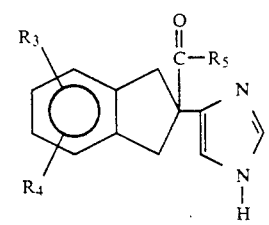 (XIX)

Reacting this compound further with an alkyl magnesium halide of formula $R_7MgHal$ gives a compound of formula

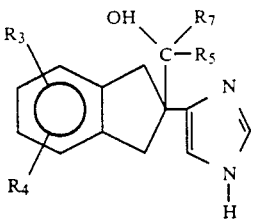 (XX)

where $R_5$ and $R_7$ are the same or different alkyl groups. As before the product can optionally be dehydrated and subsequently hydrogenated to give other compounds of formula (I).

Reduction of the acyl derivative of formula (XIX), e.g. with sodium borohydride in ethanol, gives compounds of formula (XII) from which compounds of formula (I) can be prepared as before (using method B).

Method D

In this method an alkali metal salt, e.g. sodium salt, of a 1-alkenyl-2-propanone of the formula

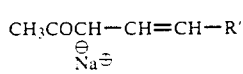 (XXI)

where R' is hydrogen or alkyl, is reacted with an α,α'-dibromo-orthoxylene of the formula

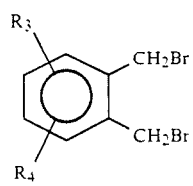 (VI)

to give a 1-[2,3-dihydro-2-(1-alkenyl)-1H-inden-2-yl]ethanone of the formula

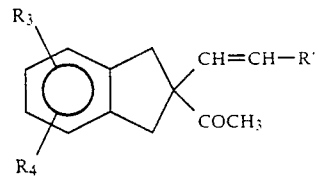 (XXII)

where $R_3$ and $R_4$ are as above.

The compound of formula (XXII) is then brominated, e.g. with bromine in a solvent which may be, for example, methylene chloride. The reaction temperature may be, for example, room temperature.

The brominated intermediate, which has the formula

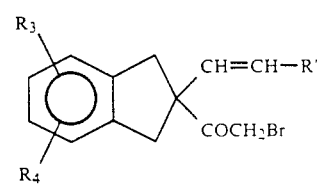 (XXIII)

is then reacted with formamide in excess formamide, preferably at 160°–180° C., to give a 4(5)-[2,3-dihydro-2-(1-alkenyl)-1H-inden-2yl]-imidazole of formula:

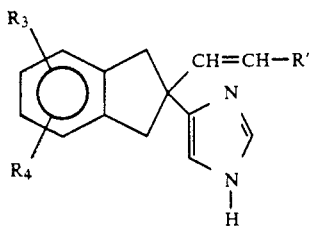

the alkenyl group R'—CH=CH— of which can, if so desired, be catalytically hydrogenated to an alkyl group so as to form a product of formula:

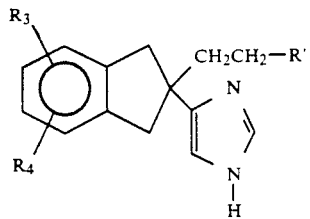

Method E

In this method, a 3-alkenoate ester of formula

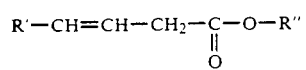

where R" is CH₃ or C₂H₅ and R' is hydrogen or lower alkyl, is reacted with an α,α'-dibromo-o-xylene of formula (VI) to give a 2,3-dihydro-2-(1-alkenyl)-1H-indene-2-carboxylate of the formula

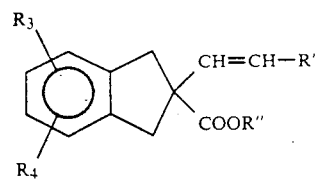

This ester can then be hydrolysed to the corresponding acid which may be converted into the acyl chloride, e.g. with thionyl chloride. Reacting the acyl chloride with ethoxy magnesium malonic acid ethyl ester of formula:

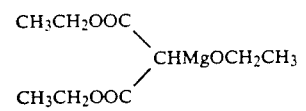

e.g. in dibutylether, and decarboxylating the intermediate obtained of formula:

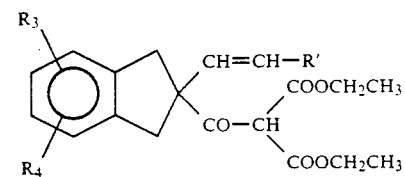

by heating in a relatively concentrated acid, e.g. sulphuric acid, solution gives a compound of the formula (XXII) which can be converted into a compound of formula (I) as in method D above.

These methods are described in more detail in the Examples below.

The following compounds of this invention have been found to be especially active α₂-antagonists:

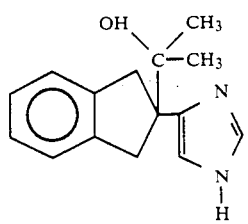

Compound I

2-[2,3-dihydro-2-[imidazol-4(5)-yl]-1H-inden-2-yl]-2-propanol

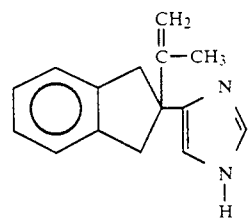

Compound II

4(5)-(2,3-dihydro-2-isopropenyl-1H-inden-2yl-)imidazole

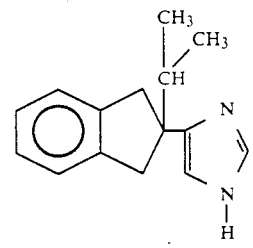

Compound III

4(5)-(2,3-dihydro-2-isopropyl-1H-inden-2-yl)imidazole

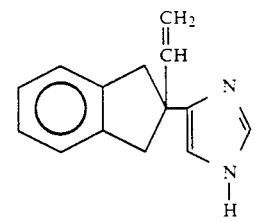

Compound IV

4(5)-(2,3-dihydro-2-vinyl-1H-inden-2-yl)imidazole

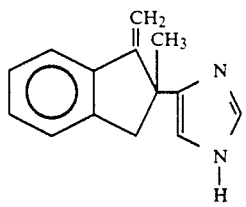

Compound V
4(5)-(2,3-dihydro-2-methyl-1-methylene-1H-inden-2-yl)imidazole

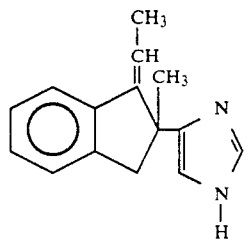

Compound VI
4(5)-(2,3-dihydro-1-ethylidene-2-methyl-1H-inden-2-yl)imidazole

The $\alpha_2$-antagonism of these compounds was determined in vitro using the isolated, electrically stimulated mouse vas deferens preparation (Marshall et al., Br. J. Pharmac. 62, 147, 151, 1978). In this model, an $\alpha_2$-agonist (detomidine) blocks electrically stimulated muscular contractions and the effect of the $\alpha_2$-antagonist is seen by administering it prior to the agonist and by determining its pA$_2$ value.

The following results were obtained

| Compound | $\alpha_2$-antagonism (pA$_2$ vs detomidine) mouse vas deferens |
| --- | --- |
| I | 5.4 |
| II | 7.0 |
| III | 6.4 |
| IV | 7.6 |

The central $\alpha_2$-blocking effect of the compounds of the invention in vivo was studied. It is known that in the rat $\alpha_2$-agonists induce dilatation of the pupil (mydriasis) and that this effect is transmitted via $\alpha_2$-receptors of the central nervous system. In an anaesthetized rat, a standard dose of detomidine was administered intravenously. Thereafter increasing doses of the antagonist under test were injected intravenously and the reversal of detomidine-induced mydriasis was observed. The ED$_{50}$ value of the antagonist, i.e. the dose producing a 50 percent reversal, was determined. This test gave the following results:

| Compound | ED$_{50}$ ($\mu$g/kg iv) |
| --- | --- |
| V | 30 |
| VI | 1 |

The clinical dosage range for the compounds of the invention may be 0.1–10 mg/kg per day for oral or intravenous administration.

The following Examples illustrate the invention.

EXAMPLE 1 a)
4(5)-(2,3-Dihydro-2-methyl-1-methylene-1H-inden-2-yl)imidazole 45 mmol of methylmagnesiumbromide was prepared in tetrahydrofuran, and added dropwise at 30°–40° C. to a tetrahydrofuran solution containing 3.0 g of 2-(imidazol-4(5)-yl)-2-methyl-1-indanone. After the addition the reaction mixture was stirred at 40° C. for an additional 2 hours and poured into acidic water.

The mixture obtained was stirred at 70° C. for 1 hour to achieve dehydration of the product and then cooled, and made alkaline with sodium hydroxide. The product, 4(5)-(2,3-dihydro-2-methyl-1-methylene-1H-inden-2-yl)imidazole, was extracted using gentle heating into methylene chloride, from which it crystallizes on standing. Yield 2.4 g (82%), m.p. 157°–164° C.

b)
4(5)-(2,3-Dihydro-1,2-dimethyl-1H-inden-2-yl)imidazole hydrochloride

The product from the previous step (2.0 g) was dissolved in 10 ml of ethanol containing 2 ml of 2N hydrochloric acid. To the solution 10% Pd/C was added as catalyst, and the solution was then stirred in a hydrogen atmosphere at room temperature until hydrogen absorption ceased. The reaction mixture was filtered, and made alkaline with sodium hydroxide, and the product was extracted with ethyl acetate. It can then be converted into the hydrochloride i a mixture of isopropanol and ethyl acetate. The product so obtained is a mixture of the cis and trans isomers and melts in the range 175°–196° C.

EXAMPLE 2 a) Ethyl 2-acetyl-2,3-dihydro-1H-indene-2-carboxylate

Tetrabutylammonium bromide (3.1 g) and 48% NaOH (90 ml) were placed in a flask. $\alpha\alpha'$-dibromo-o-xylene (50 g) in toluene (250 ml) was added to the flask, followed by ethyl acetoacetate (24.6 g) in toluene (50 ml) added dropwise. During the addition the temperature of the reaction mixture rose to 40° C. After the addition, stirring was continued for 2.5 hours. Water was added and the product was extracted into toluene. The toluene extracts were washed with water and evaporated in a rotary evaporator. 49.2 g of the product were obtained.

b) Ethyl 2-bromoacetyl-2,3-dihydro-1H-indene-2-carboxylate

Ethyl 2-acetyl-2,3-dihydro-1H-indene-2-carboxylate (43.0 g) was dissolved in methylene chloride (750 ml) and 29.8 g of bromine in methylene chloride (320 ml) was then added dropwise to the solution.

When the bromine colour had disappeared the reaction mixture was washed first with a dilute NaHCO$_3$ solution and then with water. The organic layer was dried over Na$_2$SO$_4$ and evaporated to dryness. 52.9 g of the product were obtained.

c) Ethyl 2,3-dihydro-2-[imidazol-4(5)-yl]-1H-indene-2-carboxylate

Ethyl 2-bromoacetyl-2,3-dihydro-1H-indene-2-carboxylate (44.6 g) and formamide (220 ml) were heated for 8 hours at 160° C. The reaction mixture was then poured into water (200 ml). The solution was acidified with dilute hydrochloric acid, washed with methylene chloride, and made alkaline with ammonia. The product was extracted into ethyl acetate, and the extract was washed with water, dried over MgSO$_4$ and evaporated to dryness. The yield of the crude product was 14.6 g. M.p. 147°–149° C. (from ethyl acetate).

d)
2-[2,3-Dihydro-2-[imidazol-4(5)-yl]-1H-inden-2-yl]-2-propanol hydrochloride

A Grignard reagent was prepared from magnesium turnings (0.47 g) and methyl bromide in dry tetrahydrofuran. Ethyl 2,3-dihydro-2-[imidazol-4(5)-yl]-1H-indene-2-carboxylate (1.0 g) was dissolved in dry tetrahydrofuran, and the Grignard reagent was added dropwise at 50°–60° C. to this solution. After the addition the mixture was refluxed for 2 hours. The reaction mixture was poured into acidic icewater and the tetrahydrofuran was evaporated. The aqueous solution was made alkaline with concentrated ammonia and the product was extracted in ethyl acetate. The ethyl acetate extract was dried over MgSO$_4$ and evaporated to dryness. The product (0.84 g) was converted into the hydrochloride in ethyl acetate. M.p. 148°–152° C. (from isopropanol).

e)
4(5)-(2,3-Dihydro-2-isopropenyl-1H-inden-2-yl)imidazole hydrochloride

2-[2,3-Dihydro-2-[imidazol-4(5)-yl]-1H-inden-2-yl]-2-propanol hydrochloride (0.50 g) and potassium hydrogen sulfate (2.5 g) were mixed. The mixture was heated in an oil bath at 120°–140° C. for 4 hours and stirred from time to time with a glass stick. The cooled reaction mixture was suspended in warm ethanol. The insoluble salt was filtered off and washed several times with hot ethanol. The combined ethanol solutions were evaporated and the residue was dissolved in water. The aqueous solution was made alkaline with dilute NaOH and the product was extracted with methylene chloride. The methylene chloride solution was dried and evaporated. The evaporation residue was 0.32 g. The product was converted into its HCl salt in a mixture of isopropanol and ethyl acetate. 0.20 g of the product, m.p. 203°–207° C., was obtained.

f)
4(5)-(2,3-Dihydro-2-isopropyl-1H-inden-2-yl)imidazole hydrochloride

4(5)-(2,3-Dihydro-2-isopropenyl-1H-inden-2-yl)imidazole hydrochloride (0.15 g) was hydrogenated in aqueous ethanol solution in the presence of 10% Pd/C. The charcoal was filtered off and the ethanol was evaporated. The residue was dissolved in ethyl acetate and the solution was allowed to stand for several days. The product precipitated as the hydrochloride in a yield of 0.12 g, m.p. 227°–234° C.

EXAMPLE 3 a) 2-Acetyl-2,3-dihydro-1H-indene-2-carbonitrile

Sodium (13.2 g) was dissolved in dry ethanol (220 ml). Dry diethyl ether (270 ml) was added. To the solution were simultaneously added α,α'-dibromo-o-xylene (85.2 g), dry ether (250 ml) and acetoacetonitrile (45.6 g) in dry ether (160 ml) over a period of one hour. (Acetoacetonitrile had been prepared by the method described in U.S. Pat. No. 4,152,336.) After the addition, the mixture was stirred for 1 hour at room temperature and then refluxed for 2 hours. The cooled reaction mixture wa poured into water. The ether layer was separated and the water layer was extracted once more with ether. The combined ether solutions were washed with water, dried (MgSO$_4$) and evaporated. The yield of crude product was 73.8 g.

b) 2-Bromoacetyl-2,3-dihydro-1H-indene-2-carbonitrile

2-Acetyl-2,3-dihydro-1H-indene-2-carbonitrile (32.9 g) was dissolved in diethyl ether (33 ml). Aluminium chloride (0.17 g) was added. Bromine (28.4 g) was added dropwise at room temperature and the disappearance of the bromine colour was observed. The ether solution was washed with a Na$_2$CO$_3$-solution and with water, dried over MgSO$_4$, and evaporated. 35.7 g of crude product was obtained.

c)
2,3-Dihydro-2-[imidazol-4(5)-yl]-1H-indene-2-carbonitrile hydrochloride

2-Bromoacetyl-2,3-dihydro-1H-indene-2-carbonitrile (27.8 g) and formamide (150 ml) were heated at 180° C. for 8 hours. The cooled reaction mixture wa then poured into dilute hydrochloric acid. The acidic solution was washed with methylene chloride and made alkaline with ammonia. The product was extracted into ethyl acetate. The ethyl acetate extract was washed with water, dried and evaporated. The hydrochloride of the product was made in ethyl acetate. M.p. 228°–235° C.

d)
1-[2,3-Dihydro-2-[imidazol-4(5)-yl]-1H-inden-2-yl]ethanone hydrochloride

Mg turnings (1.2 g) and dry tetrahydrofuran were placed in a flask. Methyl bromide was passed into the mixture until the Mg turnings had disappeared. The mixture was heated when necessary. 2,3-dihydro-2-[imidazol-4(5)yl]-1H-indene-2-carbonitrile (2.1 g) as the base dissolved in dry tetrahydrofuran was added dropwise to the Grignard reagent at 40°–50° C. After the addition, the mixture was refluxed for 3 hours. the reaction mixture was cooled to 0° C. and a 6M HCl solution was carefully added dropwise. The reaction mixture was then evaporated to remove the tetrahydrofuran. Water was added and the acidic solution was washed with methylene chloride. The aqueous phase was made alkaline with ammonia and the product was extracted into methylene chloride. The HCl salt was prepared in a mixture of isopropanol and ethyl acetate, m.p. 181°–184° C.

e)
1-[2,3-Dihydro-2-[imidazol-4(5)-yl]-1H-inden-2-yl]ethanol

1-[2,3-Dihydro-2-[imidazol-4(5)-yl]-1H-inden-2-yl]ethanone (0.11 g) was dissolved in dry ethanol (10 ml) and NaBH$_4$ (0.009 g) was added in small portions at room temperature. After the addition, the mixture was stirred at 40° C. for 4 hours. Part of the ethanol was evaporated and the mixture was poured into acidic water. The water was made alkaline and the product was extracted with methylene chloride. The methylene chloride solution was dried and evaporated to give the product in a yield of 0.06 g.

f) 4(5)-(2,3-Dihydro-2-vinyl-1H-inden-2-yl)imidazole 1.5 g of potassium hydrogen sulfate were mixed with 1-[2,3-dihydro-2-[imidazol-4(5)-yl]-1H-inden-2-yl]ethanol hydrochloride (0.03 g) and the mixture was stirred with a glass stick to a uniform mixture. Then the mixture was heated at 120°-140° C. for 3 hours. The cooled reaction mixture was suspended in ethanol while heating. The insoluble salts were filtered off and washed several times with hot ethanol. The combined ethanol solutions were evaporated to dryness. Water was added, the solution was made alkaline, and the product was extracted with ethyl acetate. The ethyl acetate solution was dried and evaporated to dryness to give the product.

EXAMPLE 4 a) 1-(2,3-Dihydro-2-vinyl-1H-inden-2-yl)ethanone

Tetrabutylammonium bromide (1.9 g) and 55 ml of a 48% NaOH solution were placed in a flask and $\alpha,\alpha'$-dibromo-o-xylene (30.0 g) in toluene (185 ml) was added. Then 4-penten-2-one (9.8 g) dissolved in toluene (20 ml) was added dropwise to the mixture. After the addition, the reaction mixture was stirred at 100° C. until a gas chromatogram indicated that the starting material had disappeared.

The reaction mixture was cooled and water was added. The product was extracted with toluene. The combined toluene layers were washed with water and evaporated under reduced pressure to give the product in a yield of 20.4 g.

Mass spectrogram 186 (2, $M^{+-}$), 143 (82), 142 (27), 141 (28), 129 (22), 128 (100), 127 (14), 115 (52), 91 (10), 43 (35).

$^{13}$C NMR: (20 MHz, CDCl$_3$): $\delta$26.13 (OFR q), 40.47 (2d) 63.69 (s), 115.49 (t), 124.30 (2d), 126.60 (2d), 140.13 (d), 140.59 (2s), 208.00 (s).

$^1$H NMR (80 MHz, CDCl$_3$): $\delta$2.19 (3H, s, Me), 3.05 and 3.46 (4H, AB q, J 15.6 Hz, methylene protons of the indane ring (H-1 and H-3)), 5.16 (1H, dd, J(gem) 0.7 Hz, J(trans) 17.6 Hz, one terminal methylene proton), 5.16 (1H, dd, J(gem) 0.7 Hz, J(cis) 10.3 Hz, the other terminal methylene proton), 6.02 (1H, dd, J(cis) 10.3 Hz, J(trans) 17.6 Hz, methine proton, 6.95-7.38 (4H, m, arom.).

b) 2-Bromo-1-(2,3-dihydro-2-vinyl-1H-inden-2-yl)ethanone 1-(2,3-Dihydro-2-vinyl-1H-inden-2-yl)-ethanone (5.0 g) was dissolved in methylene chloride (50 ml) and to the solution bromine (4.3 g) in methylene chloride (45 ml) was added dropwise at room temperature. When a gas chromatogram indicated that the starting material had reacted, the methylene chloride solution was washed with a dilute NaHCO$_3$-solution and then with water. The organic layer was dried with Na$_2$SO$_4$ and the solvent was evaporated at reduced pressure to give the desired product.

Mass spectrogram: 266 and 264 (1 and 1, $M^{+-}$), 185 (12), 171 (15), 167 (13), 143 (100), 142 (33), 141 (48), 129 (13), 128 (39), 127 (12), 115 (44).

c) 4(5)-(2,3-Dihydro-2-vinyl-1H-inden-2-yl)imidazole hydrochloride

2-Bromo-1-(2,3-dihydro-2-vinyl-1H-inden-2-yl)ethanone (15.0 g) and formamide (100 ml) were heated for 7 hours at 160° C. The reaction mixture was then cooled and poured into water. The water was acidified with dilute hydrochloric acid and washed with toluene. The aqueous phase was made alkaline with ammonia. The product was extracted into methylene chloride. The organic phase was washed with water, dried and the solvent was evaporated. The crude product was purified by column chromotography. The hydrochloride of the product was made in a mixture of ethyl acetate-isopropanol. M.p. 193°-197° C. (HCl-salt).

Mass spectrogram: 210 (100, $M^{+-}$), 209 (55), 195 (50), 183 (41), 182 (22), 181 (17), 168 (13), 167 (17), 166 (12), 141 (13), 129 (15), 128 (15), 127 (10), 115 (23), 104 (14), 91 (12), 81 (14).

$^{13}$C NMR (HCl-salt), (80 MHz, MeOH-d$_4$): $\delta$3.37 (4H, s, methylene protons of the indane ring (H-1 and H-3)), 4.99 (1H, dd, J(gem) 0.5 Hz, J(trans) 17.4 Hz, one terminal methylene proton), 5.17 (1H, dd, J(gem) 0.5 Hz, J(cis) 10.6 Hz, the other terminal methylene proton, 6.19 (1H, dd, J(cis) 10.6 Hz, J(trans) 17.4 Hz, methine proton), 7.07-7.32 (4H, m, arom.), 7.40 (1H, d, $^4$J 1.3 Hz, im-5(4)), 8.83 (1H, d, $^4$J 1.3 Hz, im-2).

EXAMPLE 5

4(5)-(2,3-Dihydro-2-ethyl-1H-inden-2-yl)imidazole

4(5)-(2,3-Dihydro-2-vinyl-1H-inden-2-yl)imidazole (1.0 g) was hydrogenated in the presence of 10% Pd/C in ethanol (10 ml). When the uptake of hydrogen had ceased, the reaction mixture was filtered, and the product, 4(5)-(2,3-dihydro-2-ethyl-1H-inden-2-yl)-imidazole, was obtained after evaporation.

EXAMPLE 6 a) Ethyl 2,3-dihydro-2-vinyl-1H-indene-2-carboxylate

Tetrabutylammonium bromide (0.31 g) and 48% NaOH solution (9 ml) were added to a flask. $\alpha,\alpha'$-dibromo-o-xylene (5.0 g) in toluene (15 ml) was then added to the flask. The mixture was stirred and ethyl 3-butenoate (2.16 g) in toluene (15 ml) was added dropwise at room temperature. After the addition the temperature was slowly raised to +60° C. The mixture was stirred at this temperature for 3.5 hours and then cooled. The toluene layer was separated, washed with water and evaporated at reduced pressure to give the desired product.

Mass spectrogram: 216 (17, $M^{+-}$), 143 (100), 142 (62), 141 (42), 128 (50), 115 (38).

b) 2,3-Dihydro-2-vinyl-1H-indene-2-carboxylic acid hydrochloride

Sodium hydroxide (7.99 g) was dissolved in water (80 ml) and to the solution was added dropwise ethyl 2,3-dihydro-2-vinyl-1H-indene-2-carboxylate (7.99 g) dissolved in ethanol (110 ml). After the addition, the reaction mixture was refluxed for three hours. Excess of the ethanol was evaporated, water was added, and the mixture was washed with ether. The aqueous solution was acidified with concentrated hydrochloric acid. The product was extracted into methylene chloride, and the extract was washed with water, dried and evaporated to give the product as hydrochloride salt.

$^1$H NMR (80 MHz, CDCl$_3$): $\delta$3.10 and 3.56 (4H, AB q, J 15.8 Hz, methylene protons of the indane ring (H-1 and H-3)), 5.04-5.27 (2H, m, terminal methylene protons), 6.12 (1H, dd, J(cis) 10.6 Hz, J(trans)), 17.3 Hz methine proton), 6.9-7.4 (4H, m, arom.), 9.96 (1H, broad s, —COOH).

c) 2,3-Dihydro-2-vinyl-1H-indene-2-carboxylic acid chloride

A mixture 2,3-dihydro-2-vinyl-1H-indene-2-carboxylic acid (5.09 g) and thionyl chloride (25 ml) was refluxed for 10 hours. Excess thionyl chloride was distilled off under reduced pressure. The crude product was used as such for the following reaction.

d) 1-(2,3-Dihydro-2-vinyl-1H-inden-1-yl)ethanone 1-(2,3-Dihydro-2-vinyl-1H-inden-2-yl)-ethanone was prepared by treating 2,3-dihydro-2-vinyl-1H-indene-2-carboxylic acid chloride with ethoxy magnesium malonic acid ethyl ester in dibutylether and after that with sulfuric acid according to the method of Reynolds, G.A. and Hauser, C.B., Org. Synth. 30 (1957) 70.

e) 2-Bromo-1-(2,3-dihydro-2-vinyl-1H-inden-2-yl)ethanone and 4(5)-(2,3-dihydro-2-vinyl-1H-inden-2-yl)imidazole were then prepared according to the method of Example 4 above.

EXAMPLE 7

4(5)-(2,3-Dihydro-1-ethylidene-2-methyl-1H-inden-2-yl)imidazole

Ethyl magnesium bromide (0.07 mol) in 15 ml of dry tetrahydrofuran was added into the tetrahydrofuran (20 ml) solution of 3.0 g of 2-(imidazol-4(5)-yl)-2-methyl-1-indanone at 40° C. After the addition the reaction mixture was stirred at 40° C. for 2 hours, cooled and poured into acidic water. The tetrahydrofuran was evaporated. Hydrochloric acid was added and the mixture was stirred at 70° C. to remove water, cooled and made alkaline. The product, 4(5)-(2,3-dihydro-1-ethylidene-2-methyl-1H-inden-2-yl)imidazole, was extracted with methylene chloride. Insoluble material was filtered off, and the methylene chloride was evaporated. The crude product wa dissolved in methylene chloride from which the product precipitated. Yield 2.1 g, m.p. 194°–202° C.

$^1$H NMR (80 MHz, CDCl$_3$ and some MeOH-d$_4$): δ1.54 (3H, S, CH$_3$), 2.01 (3H, d, J 7.4 Hz, =CHCH$_3$), 3.00 and 3.37 (4H, AB q, J 16.2 Hz, CH$_2$), 5.46 (1H, q, J 7.4 Hz, =CHCH$_3$), 6.81 (1H, d, $^4$J 1.0 Hz, im-5(4)), 7.15–7.70 (4H, m, arom.), 7.46 (1H, d, $^4$J 1.0 Hz, im-2).

We claim:
1. 4(5)-(2,3-dihydro-2-vinyl-1H-inden-2-yl)imidazole.

* * * * *